US007160548B2

(12) United States Patent
Gicquel et al.

(10) Patent No.: US 7,160,548 B2
(45) Date of Patent: Jan. 9, 2007

(54) ***MYCOBACTERIUM* STRAINS WITH MODIFIED ERP GENE AND VACCINE COMPOSITION CONTAINING SAME**

(75) Inventors: Brigitte Gicquel, Paris (FR); François-Xavier Berthet, Paris (FR)

(73) Assignee: Institit Pasteur, Paris (FR)

( * ) Notice: Subject to any disclaimer, the term of this patent is extended or adjusted under 35 U.S.C. 154(b) by 354 days.

(21) Appl. No.: 10/259,460

(22) Filed: Sep. 30, 2002

(65) Prior Publication Data

US 2003/0091597 A1 May 15, 2003

Related U.S. Application Data

(63) Continuation of application No. 09/463,194, filed as application No. PCT/FR98/01627 on Jul. 22, 1998, now Pat. No. 6,585,976.

(30) Foreign Application Priority Data

Jul. 22, 1997 (FR) .................................. 97 09303

(51) Int. Cl.
*A61K 39/02* (2006.01)
*A61K 39/04* (2006.01)
*A61K 39/38* (2006.01)

(52) U.S. Cl. ..................... 424/200.1; 424/9.1; 424/9.2; 424/130.1; 424/150.1; 424/164.1; 424/184.1; 424/185.1; 424/248.1; 530/300; 530/350; 536/23.1; 536/23.7

(58) Field of Classification Search .................. 424/9.1, 424/9.2, 130.1, 150.1, 164.1, 184.1, 185.1, 424/200.1, 248.1; 530/300, 350; 536/23.1, 536/23.7
See application file for complete search history.

(56) References Cited

U.S. PATENT DOCUMENTS 5,714,593 A 2/1998 Laqueyrerie et al.
6,248,581 B1 6/2001 Gicquel et al.

OTHER PUBLICATIONS

Berthet et al, "Attenuation of Virulence by Disruption of the *Mycobacterium tuberculosis erp* Gene," *Science*, Oct. 23, 1998, vol. 282, pp. 759-762.
V. Pelicic et al., "Positive Selection of Allelic Exchange Mutants in *Mycobacterium bovis* BCG", FEMS Microbiology Letters, vol. 144, pp. 161-166, (1996).
F-X Berthet et al., "Characterization of the *Mycobacterium tuberculosis erp* Gene Encoding a Potential Cell Surface Protein with Repetitive Structures", Microbiology, vol. 141, No. 9, pp. 2123-2130, (1995).
E.M. Lim et al., "Identification of *Mycobacterium tuberculosis* DNA Sequences Encloding Exported Proteins by Using phoA Gene Fusions", Journal of Bacteriology, vol. 177, No. 1, pp. 59-65, (1995).
V. Pelicic et al., "Efficient Allelic Exchange and Transposon Mutagenesis in *Mycobacterium tuberculosis*" Proc. Natl. Acad. Sci., vol. 94, pp. 10955-10960, (1997).

*Primary Examiner*—Rodney P Swartz
(74) *Attorney, Agent, or Firm*—Finnegan, Henderson, Farabow, Garrett & Dunner, L.L.P.

(57) ABSTRACT

*Mycobacterium* strains in which the erp gene is modified, and vaccine compositions comprising such *Mycobacterium* strains are provided. The modification of the erp gene may decrease the virulence and the persistence of the *Mycobacterium* strains.

21 Claims, 7 Drawing Sheets

Figure 1:
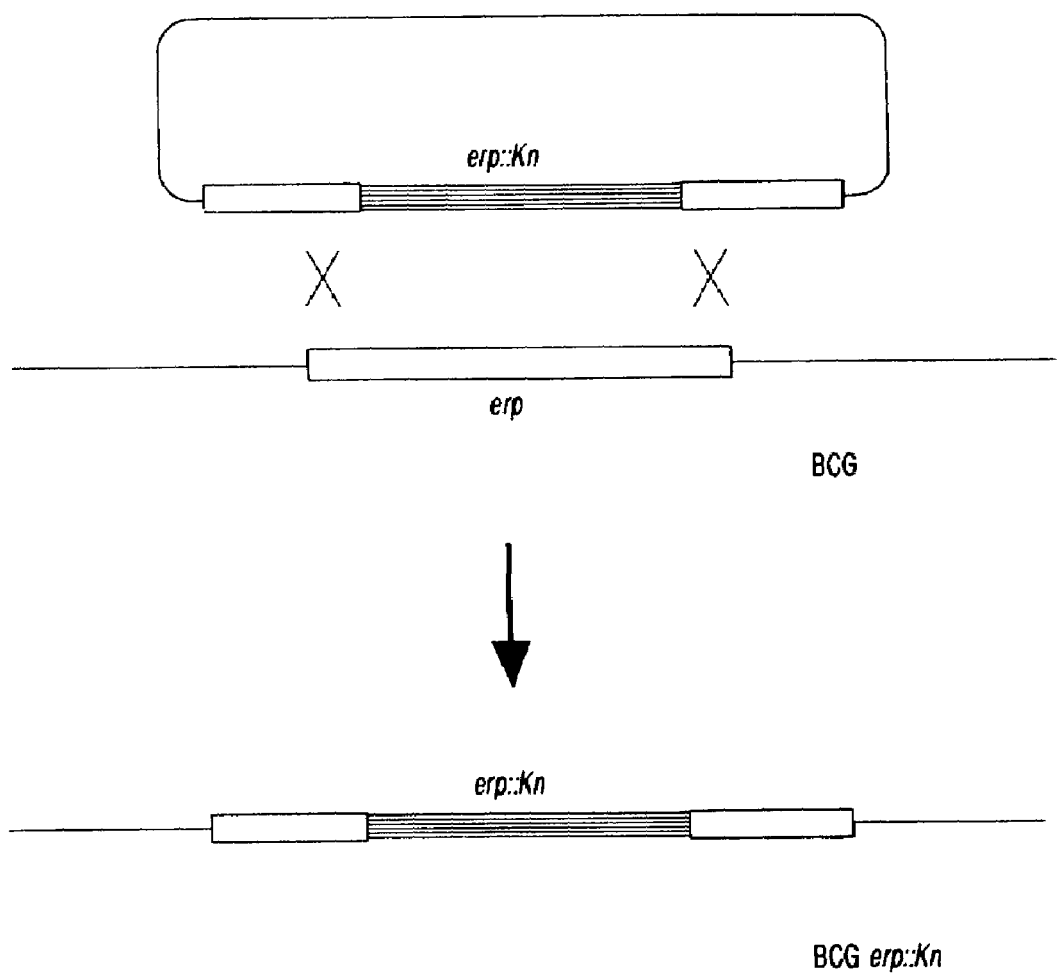

SEQUENCE LISTING

<160> NUMBER OF SEQ ID NOS: 5

<210> SEQ ID NO 1
<211> LENGTH: 5
<212> TYPE: PRT
<213> ORGANISM: Unknown Organism
<220> FEATURE:
<223> OTHER INFORMATION: Description of Unknown Organism: Illustrative
      motif
<220> FEATURE:
<221> NAME/KEY: MOD_RES
<222> LOCATION: (2)
<223> OTHER INFORMATION: Gly or Ala

<400> SEQUENCE: 1

Pro Xaa Leu Thr Ser
 1               5

<210> SEQ ID NO 2
<211> LENGTH: 6
<212> TYPE: PRT
<213> ORGANISM: Unknown Organism
<220> FEATURE:
<223> OTHER INFORMATION: Description of Unknown Organism: Illustrative
      C-terminal peptide

<400> SEQUENCE: 2

His His His His His His
 1               5

<210> SEQ ID NO 3
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 3
aaggagatct tgtgcatatt ttcttgtcta c                                31

<210> SEQ ID NO 4
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 4
aaggagatct ggcgaccggc acggtgattg g                                31

<210> SEQ ID NO 5
<211> LENGTH: 5
<212> TYPE: PRT
<213> ORGANISM: Mycobacterium bovis

<400> SEQUENCE: 5

Pro Gly Leu Thr Ser
 1               5

MYCOBACTERIUM STRAINS WITH MODIFIED ERP GENE AND VACCINE COMPOSITION CONTAINING SAME

This application is a continuation of U.S. application Ser. No. 09/463,194, filed Jan. 21, 2000 (now U.S. Pat. No. 6,585,976), which is a National Stage application of PCT/FR98/01627, filed Jul. 22, 1998, the disclosures of both of which are hereby incorporated in their entireties by reference.

The invention relates to a *Mycobacterium* strain with modified erp gene and the vaccine composition containing same.

Tuberculosis is an infectious disease caused in most cases by inhalation of bacteria belonging to the complex of *Mycobacterium tuberculosis* species (*M. africanum, M. bovis, M. tuberculosis*). With eight million new human cases annually causing three million deaths worldwide, tuberculosis remains a major public health problem (Sudre et al., 1992). The discovery of effective antibiotics (streptomycin, isoniazide, rifampicin and the like) appeared to allow the eradication of this disease. However, it is estimated that currently only 50% of patients are diagnosed and receive treatment. This treatment is often inappropriate or poorly monitored and leads to the appearance of an increasing number of antibiotic-resistant and even polychemoresistant strains (Dooley et al., 1992). In this context, the development of a vaccinal prophylaxis appears as a preferred solution for the control and eradication of tuberculosis.

The fact that an attenuated pathogenic bacterium is used as a component of a vaccine has been widely described and implemented in the prior art. The methods for obtaining such attenuated bacteria comprise the random selection of mutants induced chemically or by irradiation, or the production of recombinant bacteria of pathogenic origin in which a gene involved in a metabolic pathway has been inactivated by genetic engineering.

Straley et al. (1984) have studied the survival of avirulent mutants of *Yersinia pestis* which are deficient in one or more metabolic pathways.

Noriega et al. (1994) have manufactured, by genetic engineering, an oral Shigella strain intended to be used as a vaccine prototype by introducing deletions into a gene (aroA) encoding a protein involved in a metabolic pathway for an aromatic amino acid and they have demonstrated that the resulting defective recombinant *Shigella* strains were capable of inducing protective antibodies against the wild-type pathogen.

A major study has also been carried out using *Salmonella* as a model. See for example the reports by Hoiseth et al. (1981), Levine et al. (1987), Oyston et al. (1995) and Curtiss (1990).

However, similar studies have not yet been carried out for *Mycobacterium tuberculosis*, the etiological agent of tuberculosis (TB), which infects a third of the world population and kills three million people per year. Tuberculosis is the most important cause of mortality in the world caused by a group of infectious organisms (Bloom and Murray, 1992) grouped under the name "*M. tuberculosis complex*". According to the WHO, more people died of tuberculosis in 1995 than during any previous year. It has been estimated that up to half a billion people will suffer from tuberculosis in the next 50 years. However, in spite of its importance, the genetic determinants of the virulence and persistance of *M. tuberculosis* remain scarcely characterized.

Indeed, the virulence of pathogenic mycobacteria is associated with their ability to grow and persist at the intracellular level. Bacteria of the *M. tuberculosis* complex parasitize the phagocytic cells in which they live and multiply in a specialized vacuolar compartment called the phagosome. The phagosomes containing live *M. tuberculosis* do not acidify and escape fusion with the lysosomes. The mechanisms by which *M. tuberculosis* make their phagosome more hospitable remain unknown and the mycobacterial genes affecting their intracellular growth and multiplication are being actively investigated.

The extreme difficulty of creating defined mutants of *M. tuberculosis*, either by allelic exchange or by transposon mutagenesis, has prevented the identification of these virulence factors according to the postulates of Koch (Falkow, 1988; Jacobs, 1992). Alternative genetic strategies have been used instead, including the complementation of a non-pathogenic bacterium (Arruda et al., 1993) and of spontaneous avirulent mutants with virulent *M. tuberculosis* (Pascopella et al., 1994) and virulent *M. bovis* (Collins et al., 1995) chromosomal DNA libraries. Although these studies have identified genes potentially involved in the entry into the epithelial cells and conferring a growth advantage in vivo, the great majority of the mycobacterial genes involved in the virulence and survival in the host organism remain unknown. The development of effective mutagene systems is therefore the priority for mycobacterial genetics.

One method for the creation of mutants is allelic exchange mutagenesis. Recently, allelic exchanges taking place with a low frequency have been demonstrated in bacteria of the *M. tuberculosis* complex using a suicide vector (Reyrat et al., 1995; Azad et al., 1996) and novel protocols allowing easier detection of the allelic exchange mutants have also been developed (Norman et al., 1995; Balasubramamian et al., 1996; Pelicic et al., *FEMS Microbiol. Lett.* 1996). However, the detection of a very rare allelic exchange event is prevented by low transformation efficiencies and the high frequency of illegitimate recombinations. Thus, many *Mycobacterium* genes still remain refractory to allelic exchange by means of the available technologies.

More particularly, the allelic exchange mutagenesis systems require the use of more efficient methods. The problems encountered may be overcome by the use of a replicative vector which is effectively conditionally lost. The possibility of introducing such vectors makes it possible to avoid the problems resulting from the low transformation efficiencies. Thus, under counterselection conditions, the clones still containing the vector are eliminated, thus allowing the detection of very rare genetic events. Such a system has been recently developed. Using a replicative vector under certain conditions which is lost at 39° C. in *M. smegmatis*, the first library of mycobacterial insertion mutants was constructed in this rapidly growing model strain (Guilhot et al., 1994). However, the heat-sensitive vectors used are only slightly heat-sensitive in slow-growing mycobacteria of the *M. tuberculosis* complex and therefore cannot be used in these species for allelic exchange mutagenesis (unpublished data).

The inventors have succeeded in altering the virulence and the persistance of *Mycobacterium* strains in the host cells.

They have indeed produced a *Mycobacterium* strain one gene of which has been modified so as to attenuate its virulence.

Modified gene is understood to mean a gene which has undergone a modification abolishing the production of the corresponding protein or allowing the production of a protein which is at least 20% different in terms of activity compared with the natural protein.

BCG (Bacille Calmette-Guérin), an avirulent strain derived from *M. bovis*, is widely used worldwide as a vaccine against tuberculosis. However, while BCG can be administered without any problem to individuals with no immune deficiency, the same is not true for immunosuppressed individuals such as people infected with the AIDS virus, people who have had a marrow transplant, people suffering from a cancer, or people with altered functioning of one of the components of the immune system.

That is the reason why the present invention relates to a *Mycobacterium* strain with limited persistance.

The gene modified in the *Mycobacterium* strain in accordance with the invention is the erp gene. It may also be a gene having a complementation homology (of at least 80%) with the erp gene.

Analysis of the deduced protein sequence of the erp gene shows that the latter encodes a protein whose calculated molecular mass is 28 kDa. The presence of a signal sequence for export at an N-terminal position as well as the existence of a C-terminal hydrophobic region suggest that the molecule can be anchored in the plasma membrane or located at the surface of the bacilli. Furthermore, the central region of the protein comprises two repeat regions each composed of 6 copies of a P(G/A)LTS (SEQ ID NO 1) motif positioned in tandem. This organization is similar to that found in many surface proteins associated with peptidoglycan in Gram-positive bacteria and in *Plasmodium*.

A genetic methodology allowing the selection and the identification of DNA fragments encoding exported proteins has recently been adapted for *M. tuberculosis* in the laboratory. This system is based on the production of libraries of *M. tuberculosis* DNA fragments fused with the *E. coli* alkaline phosphatase (phoA) gene lacking expression and export signals. Alkaline phosphatase (PhoA) possesses detectable enzymatic activity only after export across the plasma membrane. Using this system, several DNA fragments allowing the export of PhoA in mycobacteria have been selected in the presence of a chromogenic substrate, and partially sequenced. One of the fusions carried by the recombinant plasmid pExp53 exhibits sequence similarities with an *M. leprae* gene which encodes a protein of 28 kDa, potentially located at the surface of the bacillus. Furthermore, this protein is a major *M. leprae* antigen recognized by the sera of lepromatous leprosy patients (WO 9607745). We have furthermore determined, by molecular hybridization experiments, that the erp gene is unique in the *M. tuberculosis* genome and that it is also present in the genome of the other members of this complex of species (*M. africanum, M. bovis, M. bovis* BCG).

To allow the study of ERP and to confirm its localization at the surface, specific anti-ERP antibodies were produced. For that, the ERP protein fused with the maltose-binding protein (MalE/MBP) or fused with a C-terminal peptide containing 6 histidine residues (SEQ ID NO 2) was produced. This strategy made it possible to obtain, in a large quantity, recombinant ERP-MalE and ERP(His) 6 proteins expressed in *Escherichia coli*. The purification of these molecules was carried out using the techniques of affinity chromatography on a resin of amylose (MalE system) or of chelated nickel (Histidine system). The relative molecular weight, determined by SDS-PAGE electrophoresis, is 36 K. The difference with the theoretical molecular weight may be attributed to a delay in electrophoretic migration due to the high content (15%) of proline residues. A protocol for immunizing rabbits with the aid of the purified ERP-MalE and ERP(His)6 chimeras made it possible to obtain polyclonal sera at a high titer which allow the specific detection of the ERP protein.

With the aid of the antisera obtained in rabbits, the localization of the ERP protein in *Mycobacterium tuberculosis* was specified. Electron microscopy observations after immunolabeling with colloidal gold made it possible to detect the presence of the ERP protein at the surface of tubercle bacilli derived from an in vitro culture. Thus, the ERP protein is capable of exhibiting at the surface of the mycobacteria epitopes of other antigens and for vaccinal or therapeutic purposes. Furthermore, similar experiments have made it possible to detect the ERP protein in murine macrophages infected with *M. tuberculosis*.

To analyze the function of the ERP protein, a BCG strain in which the erp gene was modified by allelic exchange was constructed. The survival of this strain in comparison with the wild-type strain was analyzed in the mouse model. It was demonstrated that the mutation of the erp gene severely affects the persistance of *M. bovis* BCG. This reduction in persistance is observed in all the organs tested (spleen, liver, lungs). In addition to the role of the gene in the BCG survival process, these observations mean that the erp gene is expressed during the growth phase in vivo in the host.

More particularly, the modification of the erp gene is carried out by mutation, insertion, deletion or substitution; the modification of at least one base pair is sufficient.

According to an advantageous embodiment of the strain in accordance with the invention, the erp gene is modified by insertion of a nucleotide or polynucleotide which may be a selectable gene. This gene may in particular encode the resistance to an antibiotic such as kanamycin, spectinomycin or hygromycin.

The preferred *Mycobacterium* strains are those belonging to the *Mycobacterium* genus, preferably to the *Mycobacterium tuberculosis* complex and still more preferably to the *Mycobacterium tuberculosis* species or to the *Mycobacterium bovis* species.

The present invention relates more particularly to the BOG erp::Kn strain also called BCG erp::aph (Collection Nationale de Cultures de Microorganismes ("CNCM"), located at Institut Pasteur, 28, Rue du Docteur Roux, F-75724 PARIS CEDEX 15, France, Deposit No. I-1896, made Jul. 15, 1997) or a variant incapable of expressing the product of the active erp gene as well as the *M. tuberculosis* H37Rv erp::aph strain (CNCM Deposit No. 1-2048, made jun. 29, 1998) or a variant incapable of expressing the gene product.

The invention also relates to a *Mycobacterium* strain whose erp gene is modified and which is capable of producing, following recombination events, epitopes or antigenic determinants capable of immunizing and/or protecting against pathogenic agents such as infectious agents or cancer genes, or of producing molecules leading to a modulation of the immune system such as cytokines, chemokines, soluble receptors for molecules interacting with agents leading to a pathological condition or inducers of immune responses such as IL2, IL4, IL10 or IL12 (in humans or animals).

The present invention therefore also relates to a *Mycobacterium* strain as described above which is capable, in addition, of expressing a polynucleotide encoding a mycobacterium antigen of a species other than that to which said strain belongs, it being possible for the polynucleotide in question to be foreign to the *Mycobacterium* genus.

A subject of the invention is also a purified polynucleotide comprising a modified erp gene and a fragment of at least 60 nucleotides corresponding to the whole or part of a gene encoding an exported antigen of the *Mycobacterium* genus or encoding an antigen foreign to the *Mycobacterium* genus.

The modification of the erp gene may be obtained, for example, by addition, insertion or modification of nucleotides. In the context of the invention, the selection of the *Mycobacterium* strain whose erp gene is thus modified may be carried out by gene amplification and nucleotide sequencing or RFLP of the nucleic region mutated in said strain isolated on agar according to the counterselection protocol in the presence of sucrose (Pelicic et al., 1996), for example. An alternative consists in carrying out hybridizations under high stringency conditions (Berthet et al., 1995) characterized by the use of a probe corresponding to the whole or part of the erp gene which has been genetically modified but which conserved at least 20% of its activity and which preferably hybridizes with the whole or part of the modified gene present in the desired strain.

The modification of the erp gene may also be carried out by means of a recombinant vector comprising the inactivated erp gene. This vector is used for the transformation of a *Mycobacterium* strain and should allow an allelic exchange with the wild-type erp gene with the aim of modifying it.

Advantageously, the vector in accordance with the invention comprises a replication origin which is heat-sensitive in mycobacteria. It may also comprise the counterselectable sacB gene optionally with a gene allowing positive selection such as a gene encoding resistance to an antibiotic.

The modification of the erp gene in the vector in accordance with the invention may be carried out as described above.

More particularly, said vector corresponds to the recombinant plasmid pIPX56 (CNCM Deposit No. I-1895, made Jul. 15, 1997). Indeed, this plasmid consists of an *E. coli*—mycobacteria shuttle cloning vector of the pPR27 type (CNCM Deposit No. I-1730, made Jun. 19, 1996) comprising a replication origin which is heat-sensitive in mycobacteria, the counterselectable sacB gene and conferring resistance to gentamycin. In the plasmid pIPX56, an insertion of 5.1 kb of a PstI fragment was carried out at the level of the unique PstI site of pPR27. This 5.1 kb fragment corresponds to a 3.9 kb DNA fragment of *M. tuberculosis* comprising the erp gene, into which a cassette (1.2 kb) conferring resistance to kanamycin has been inserted. This plasmid therefore makes it possible to carry out allelic exchange experiments at the level of the erp locus in mycobacteria.

In the context of the present invention, it is also advantageous to be able to have a vector derived from pIPX56 comprising the unmodified erp gene.

The subject of the invention is therefore also the use of a recombinant vector as described above for the preparation of a *Mycobacterium* strain in accordance with the invention by allelic exchange.

Another subject of the invention is a method for the production of a *Mycobacterium* strain as described above comprising the steps of:
  transforming, with a vector as described above, a *Mycobacterium* strain propagated at a permissive temperature,
  culturing the colonies resulting from the transformation on a medium supplemented with a selectable product and sucrose,
  isolating the recombinant strain.

According to an advantageous embodiment of the method in accordance with the invention, the selectable product is an antibiotic such as kanamycin, spectinomycin or hygromycin.

By way of example, a recombinant *Mycobacterium* strain is produced in accordance with the invention as follows:
  a) the plasmid pIPX56 is introduced by electroporation into a strain of the *Mycobacterium tuberculosis* complex propagated at a permissive temperature (32° C.). This step makes it possible to have a population of bacteria in which each individual possesses several copies of the erp::Kn cassette;
  b) a colony resulting from the transformation is cultured in liquid medium at 32° C. for 10 days, and then the culture is inoculated on plates containing kanamycin (50 mg/ml) and 2% sucrose (weight/vol.) which are incubated at a nonpermissive temperature at 39° C. This step makes it possible to enrich in double homologous recombination events by counterselection and elimination of the integrations of vectors (single homologous recombination or illegitimate recombination).

The invention also relates to an immunogenic composition comprising a *Mycobacterium* strain in accordance with the invention or obtained by carrying out the method mentioned above.

It also relates to a vaccine composition comprising a *Mycobacterium* strain in accordance with the invention or obtained by carrying out the method mentioned above, in combination with at least one pharmaceutically compatible excipient.

This vaccine composition is intended for the immunization of humans and animals against a pathogenic strain of mycobacteria and comprises an immunogenic composition as described above in combination with a pharmaceutically compatible excipient (such as a saline buffer), optionally in combination with at least one immunity adjuvant such as aluminum hydroxide or a compound belonging to the muramyl peptide family.

To obtain an adjuvant effect for the vaccine, many methods envisage the use of agents such as aluminum hydroxide or phosphate (alum) which are commonly used as a solution titrating 0.05 to 0.01% in a phosphate-buffered saline, mixed with synthetic polymers of sugar (Carbopol) as a 0.25% solution. Another suitable adjuvant compound is DDA (2 dimethyldioctadecylammonium bromide), as well as immunomodulatory substances such as the lymphokines (for example gamma-IFN, IL-1, IL-2 and IL-12) or also gamma-IFN-inducing compounds such as poly I:C.

The vaccine composition in accordance with the present invention is advantageously prepared in injectable form, for administration orally or by inhalation, or in liquid solution or in suspension; suitable solid forms intended to be prepared in solution or in liquid suspension before injection can also be prepared.

Furthermore, the vaccine composition may contain minor components of an auxiliary substance such as wetting or emulsifying agents, agents for buffering the pH or adjuvants which stimulate the efficacy of the vaccines.

The vaccine compositions of the invention are administered in a manner compatible with the dosage formulation and in a therapeutically effective and immunogenic quantity. The quantity to be administered depends on the subject to be treated, including, for example, the individual capacity of their immune system to induce an immune response.

The vaccine dosage will depend on the route of administration and will vary according to the age of the patient to be vaccinated and, to a lesser degree, the size of this patient. Preferably, the vaccine composition according to the present invention is administered by the intradermal route in a single portion or by the oral route or by aerosol.

In some cases, it will be necessary to carry out multiple administrations of the vaccine composition in accordance with the present invention without, however, generally exceeding six administrations, preferably four vaccinations. The successive administrations will normally be made at an interval of 2 to 12 weeks, preferably of 3 to 5 weeks. Periodic boosters at intervals of 1 to 5 years, preferably 3 years, are desirable in order to maintain the desired level of protective immunity.

The invention also relates to a diagnostic method which makes it possible to discriminate between individuals, on the one hand, who have been vaccinated with the aid of a *Mycobacterium* strain no longer producing active ERP and, on the other hand, those who have had a natural infection or a vaccination with the aid of a strain producing the natural ERP protein.

Indeed, the individuals who have had a vaccination with a *Mycobacterium* strain no longer producing the natural ERP protein can be distinguished by the absence, from a biological sample such as for example serum, of antibodies directed against ERP and/or by the absence of T reactivity (measured for example during a test of proliferation or a test of secretion of cytokines or CTL test) against the purified ERP protein. An alternative also consists in testing for a differential reactivity with the aid of antibodies directed against the unmodified part of the natural ERP protein compared with the corresponding part of the mutated ERP protein.

The subject of the present invention is therefore also a method of screening individuals, to whom a vaccine composition in accordance with the invention has been administered, comprising detecting the absence, from a biological sample from said individuals, of antibodies or of T cells directed against the whole or part of the purified ERP protein, it being possible for the biological sample to be blood.

The subject of the invention is also a composition comprising the modified ERP protein.

Another aspect of the present invention relates to the repeat sequences present in the erp gene in particular of the strains of the *M. tuberculosis* complex. Indeed, in the majority of the cases studied by the Inventors, the tuberculosis patients did not develop a humoral response against erp. The mice vaccinated with BCG do not develop a humoral response against erp either. By contrast, the leprosy patients develop a strong response against erp. The major difference between the ERP protein from *M. tuberculosis* and the similar protein from *M. leprae* lies in the absence of repeats in *M. leprae*.

Consequently, the repeats may be responsible for the blocking of the humoral response specifically against erp or even, in general, against other antigens. It is indeed known that tuberculosis patients develop only a weak humoral response at the beginning of the tuberculosis disease. It could therefore be possible to use the repeats carried by erp to inhibit the development of a specific humoral response by combining these repeats with any antigen against which it is desired to avoid a humoral response being induced or perhaps even used by these repeats to inhibit any humoral response in some advantageous contexts. This type of strategy could be appropriate for the following situations: avoiding the development of the humoral response against viral vaccine vectors (see table).

Thus, the present invention relates to the use of the repeat sequences of the erp gene, optionally in combination with at least one other antigen, for inhibiting the development of a humoral response.

It also relates to a vector for expression in a microorganism, characterized in that it comprises a nucleotide sequence encoding the ERP protein lacking its repeat sequences. The microorganism harboring the expression vector may be, for example, *E. coli* or any other organism which may be suitable for the expression of a nucleotide sequence encoding the ERP protein lacking its repeat sequences, including the mycobacteria.

The subject of the present invention is also a strain of mycobacteria, characterized in that the erp gene lacks its repeat sequences. Indeed, such a strain, having ERP with no repeats, would be immunogenic while having a protective effect.

Furthermore, the subject of the present invention is a purified recombinant ERP protein preferably produced by *E. coli*. Advantageously, this recombinant protein comprises six histidine residues at its C-terminal end.

FIG. 1 represents the production of a BCG strain whose erp gene was inactivated by insertion of a cassette for resistance to kanamycin.

FIG. 2 represents the number of cfu persisting in each of the relevant organs as a function of the number of days following the intravenous injection of either the wild-type BCG or the mutant BCG (BCG erp::Kn also called BCG erp::aph).

FIG. 3 represents the number of cfu resulting from the multiplication of the parental BCG (1173P2) and of the mutated BCG (erp::aph) in cultures of macrophages derived from BALB/C mouse medullary precursors.

FIG. 4 represents the number of cfu resulting from the multiplication of the parental (wt), mutated (ERP$^-$) and complemented strains of BCG and H37Rv in cultures of macrophages derived from Balb/c mouse medullary precursors.

FIG. 5 represents the comparison of the number of cfu resulting from the multiplication of the parental, mutated and complemented BCG, on the one hand, with that of the parental, mutated and complemented H37Rv, on the other hand, in cultures of macrophages derived from Balb/c mouse medullary precursors, as a function of the organs (lungs, spleen or liver).

The invention is not limited to the above description and will be understood more clearly in the light of the examples.

Materials and Methods

Production and Purification of Recombinant ERP Protein

The region encoding ERP deprived of its signal sequence was amplified by PCR by means of the oligonucleotide primers His-2 (5'-AAGGAGATCTTGTGCATATTTTCTTGTCTAC-3') (SEQ ID: 3), and His-3 (5'-AAGGAGATCTGGCGACCGGCACGGTGATTGG-3') (SEQ ID: 4); digested with BglII and cloned into the BamHI site of the expression plasmid pQE70 (QIAGEN GmbH, Hilden, Germany). The resulting plasmid, designated pHis233, was subjected to electroporation into the *Escherichia coli* M15 strain.

Two liters of cultures of the *Escherichia coli* M15 strain (pHis233) were grown in a Luria-Bertani broth, induced with ITPG and were treated for the purpose of protein purification under denaturing conditions using a nickel-nitrilotriacetic acid (NTA) agarose resin as described by the supplier (QIAGEN GmbH). Eluted ERP-His6 was dialyzed twice for 12 hours with PBS and stored in the cold at −20° C. Two rabbits (New Zealand strain) were immunized with 100 μg of protein and then every fifteen days with 150, 200 and 250 μg of ERP-His6 emulsified in incomplete Freund's adjuvant. The hyperimmune anti-ERP sera were obtained by bleeding the animals six weeks after immunization. The separation by SDS-PAGE electrophoresis and immunoabsorption were carried out as described in J. Sambrook et al., 1987.

Immunocytochemistry (Full Setup)

Cells were fixed with a 0.1 M buffer of paraformaldehyde at 1%, washed in the same buffer and then applied to a nickel grid coated with Formvar carbon, previously made hydrophilic by the "glow discharge" electrical process. The grids were then prepared by immunocytochemistry, rinsed with distilled water and negatively stained with 1% ammonium molybdate in water.

Cryosections

The bacteria or infected macrophages (m.o.i.=1) were fixed with 2% paraformaldehyde and 0.2% glutaraldehyde in 0.1 M phosphate buffer. The cells were harvested and entrapped in gelatin at 10%. The agglomerated cells were incubated from two hours to a whole night in 1.8 M sucrose and polyvinylpyrrolidone at 15% (MW 10,000). Small blocks were mounted on "object holders", cooled in liquid nitrogen and cryosectioned at −120° C. with a Reickert FCS cryo-ultamicrotome. Thin sections were then recovered in a drop of 2.3 M sucrose and applied to Formvar carbon-coated nickel grids. The grids were then treated for immunocytochemistry, then rinsed with distilled water and included in methyl cellulose containing 0.3% uranyl acetate.

Immunocytochemistry

Grids were treated with drops of the following reagents: $NH_4Cl$ (50 mM) in PBS, 10 minutes, Bovine Serum Albumin (BSA) 1% (w/v) in PBS, 5 minutes, an anti-ERP antiserum diluted 1/100 in PBS-BSA, 1 hour, PBS-BSA (three washes of 2 to 5 minutes each), conjugated with gold anti-rabbit IgG antibody (H+L chains) (grains of 10 nm or 5 nm in size, British Biocell International, UK) diluted 1/20 in gelatin from fish skin PBS-0.1% (Sigma), 30 to 45 minutes, PBS (one wash, 1 minute) and distilled water (three washes of one minute each). The examples were then fixed with 1% glutaraldehyde in 0.1 M cacodylate buffer (pH 7.4) for 2 minutes.

Inactivation of the erp Gene

A DNA fragment of 3.9 kb comprising the full length of the erp gene was cut from pIX412 by a PstI digestion and cloned into the corresponding site of pACYC177. The resulting plasmid, designated pPB1, was linearized with EcoRI which cuts at a unique site inside erp. In parallel, an aph cassette conferring resistance to kanamycin was cut by PstI digestion in the plasmid pUC-4K. pPB1 and the aph fragment were cut with T4 DNA polymerase (Boehringer Mannheim) as recommended by the manufacturer, and ligated together to give pPB2. A DNA fragment of 5.2 kb containing erp::aph was cut from pPB2 by PstI digestion and cloned into nonreplicative pJQ200 giving rise to the vector pPB3. Five µg of pPB3 were subjected to electroporation into M. bovis BCG which was then plated on Middelbrook 7H11 plates supplemented with kanamycin (20 µg/ml). Colonies were sorted by PCR with oligonucleotides flanking the EcoRI sites used for the insertion of aph and transferred (replica spotting) to plates containing kanamycin (20 g/ml) and 2% sucrose. A clone containing an insert of 1.3 kb and more sensitive to sucrose was analyzed by Southern blotting as described in Berthet et al., 1995.

Mice were kept and handled according to the directives of Institut Pasteur for the breeding of laboratory animals. The macrophages derived from the spinal cord were isolated from seven-week old femurs, from female BALB/c mice. The cells were inoculated at $5\times10^5$ cells per well into Labtek™ 8-well culture chambers (Nunc) and were cultured for seven days as described in Chastellier et al., 1995.

The counting of the CFUs was carried out as described in Lagranderie et al., 1996.

EXAMPLE 1

Generation of Anti-ERP Rabbit Polyclonal Sera

Four female New Zealand rabbits were immunized the first time with 100 µg of ERP(his)6 protein. Secondary immunizations (boosters) were performed every 15 days with 150, 200 and then 250 µg of purified protein. From two months after the first immunization, the sera collected had a sufficient titer to be used for the immunodetection in Western blotting and by immunohistochemistry in electron microscopy. For the electron microscopy immunohistochemistry experiments, the sera were purified by adsorption/elution on nitrocellulose strips containing ERP.

EXAMPLE 2

Construction of a BCG erp::Kn Strain

A M. tuberculosis DNA fragment of 3.9 kbp containing the erp gene was obtained by PstI digestion of the plasmid pIPX412 (CNCM No. I-1463) (Berthet et al., 1995). This fragment was introduced into the cloning vector pACYC177, giving rise to the plasmid pPB1. The plasmid pPB1 was then linearized with the restriction enzyme EcoRI, cutting once at the level of a site situated in the erp gene. In parallel, a genetic cassette (aph) which is small in size (1.3 kbp), conferring the resistance to the antibiotic kanamycin, was prepared by restricting the plasmid pUC-4K with PstI. The pACYC177/EcoRI and aph/PstI fragments were treated, under the conditions described by the supplier, with the Klenow fragment of DNA polymerase I of Escherichia coli and with the T4 phage polymerase, respectively, in order to generate fragments with blunt ends. These two fragments were then ligated and transformed in E. coli. A recombinant plasmid having inserted the aph cassette at the level of the erp gene was selected by colony hybridization and called pPB2. The fragment containing erp::aph was then excized from pPB2 by PstI digestion and introduced into the vector pJQ200 possibly allowing counterselection in the presence of sucrose. The resulting plasmid was called pPB3. Plasmid pPB3 (three micrograms) was introduced into the Mycobacterium bovis BCG Pasteur 1173 P2 strain by electroporation (Gene pulser BioRad, 2500V, 200Ω, 25 µF). The transformed cells were incubated for 24 hours at 37° C. in 7H9 medium (5 ml) and then plated on 7H11 plates containing kanamycin (20 µg/ml). The plates were incubated for 25 days at 37° C. and thirty colonies of bacteria resistant to kanamycin were subcloned individually both by PCR using a pair of oligonucleotides flanking the EcoRI site of the erp gene, and by Southern blotting using an internal erp probe. A recombinant clone, called BCG erp::Kn, was selected on the following criteria:

1—by PCR, disappearance of the band corresponding to the wild-type allele (500 bp) for the mutant BCG erp::Kn. Production of a PCR amplification fragment of 1800 bp (500+1300) signing the insertion of the aph cassette into the genomic copy of the erp gene;

2—by Southern blotting, detection of a signal for hybridization at 5.2 kbp with the DNA of BCG 13K instead of 3.9 kbp for the wild-type BCG. Loss of the EcoRI site internal to the erp::aph gene.

EXAMPLE 3

Test of the Persistence of BCG erp::aph in Mice

A bacterial stock stored at −70° C. of the BCG erp::Kn strain was produced in the following manner: a colony grown on 7H11+Kn (20 µg/ml) was inoculated on potato/Sauton medium in the presence of kanamycin (20 µg/ml) until a film is formed. This film will be used to produce an inoculum (10 µg/ml) for flasks containing liquid Sauton medium. After 8 days of growth, the film thus formed in Sauton is recovered, ground and is resuspended in Beck-Proskauer medium supplemented with 6% glycerol (Vol./Vol.). The stock thus obtained titrated $4.8 \times 10^8$ colony forming units (CFU)/ml.

Figure 2A:
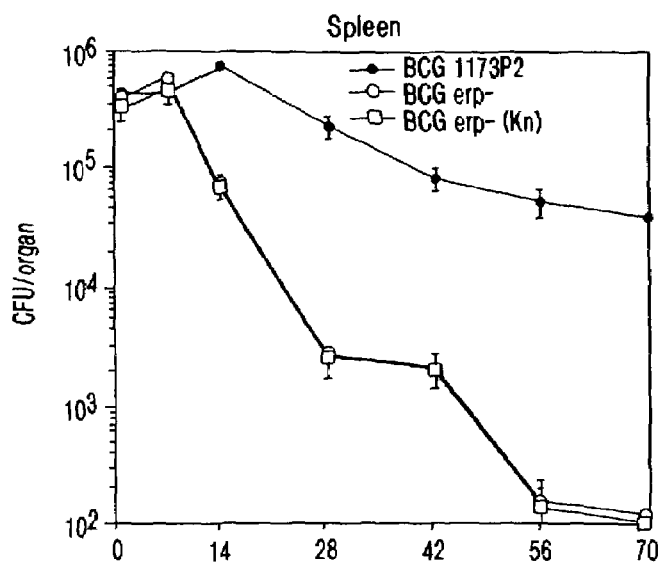
Figure 2B:
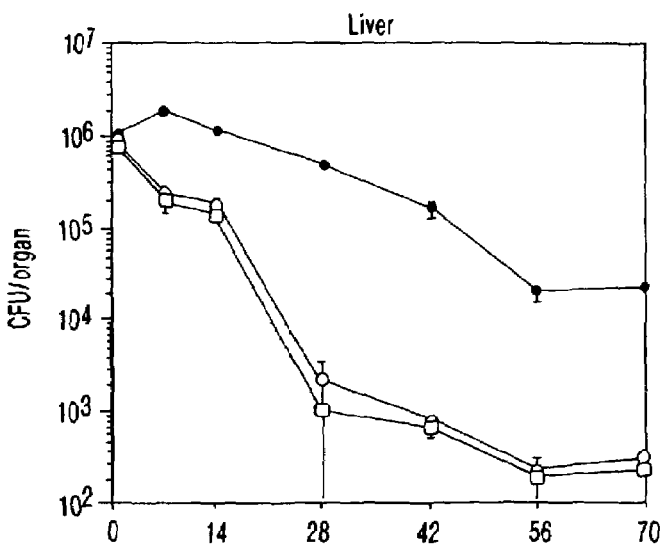
Figure 2C:
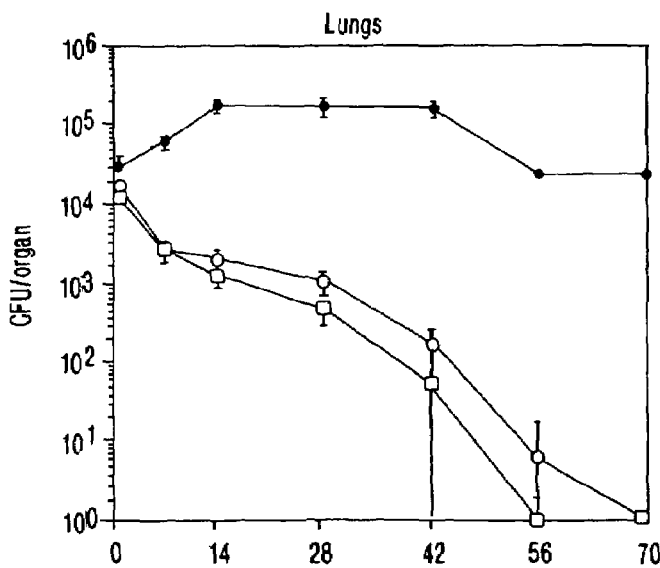

With the aid of this stock, BALB/c mice were injected intravenously with $10^6$ cfu of wild-type BCG and mutant BCG (BCG erp::Kn) in suspension in PBS. Three organs, the spleen, the liver and the lungs, were removed in a sterile manner at days 1, 7, 14, 28, 42, 56 and 70. At each point, the organs were ground in Beck-Proskauer medium and the bacteria were inoculated at different dilutions on 7H11 plates with or without kanamycin (20 µg/ml). The number of viable bacteria present in the different organs as a function of time was determined by counting the CFUs (FIG. 2).

EXAMPLE 4

Figure 3:
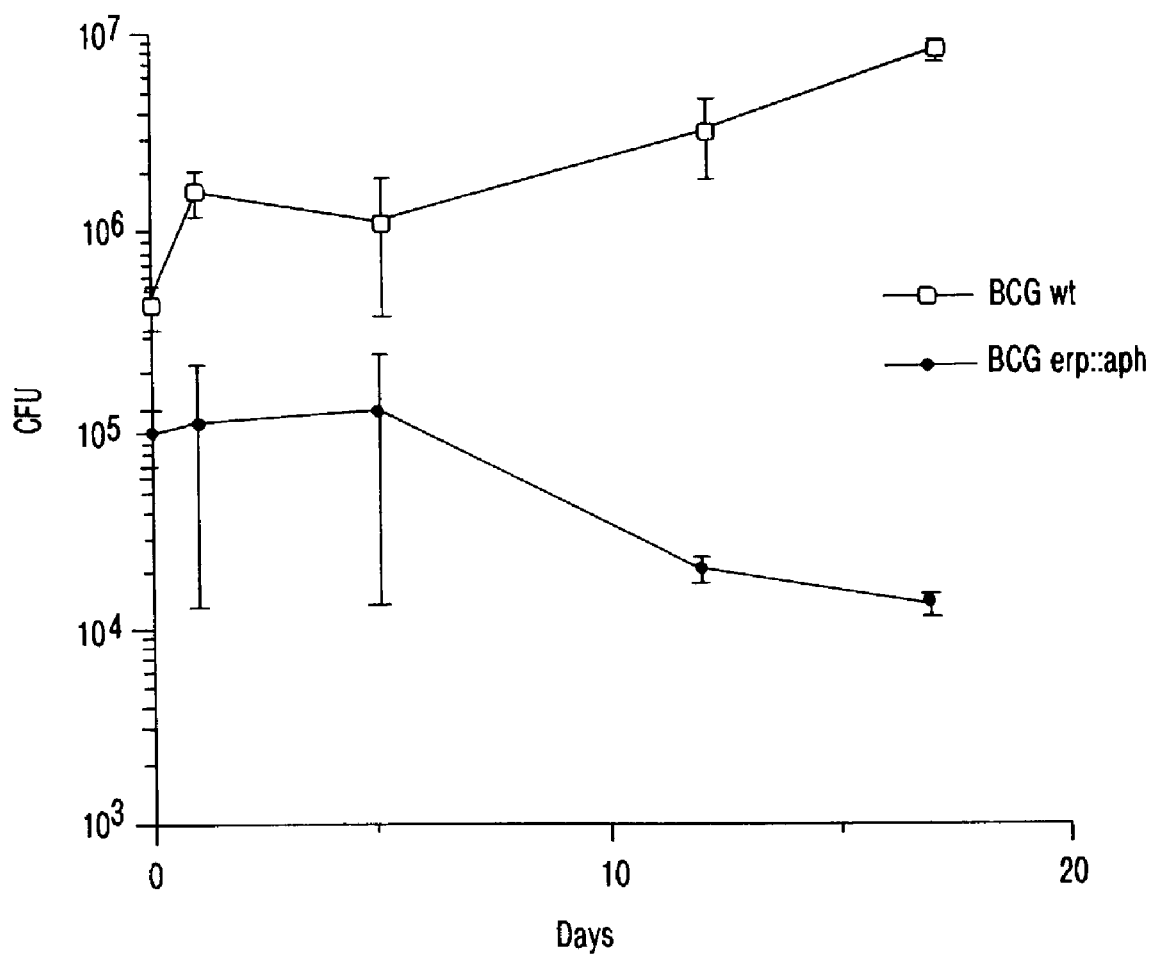
Figure 4:
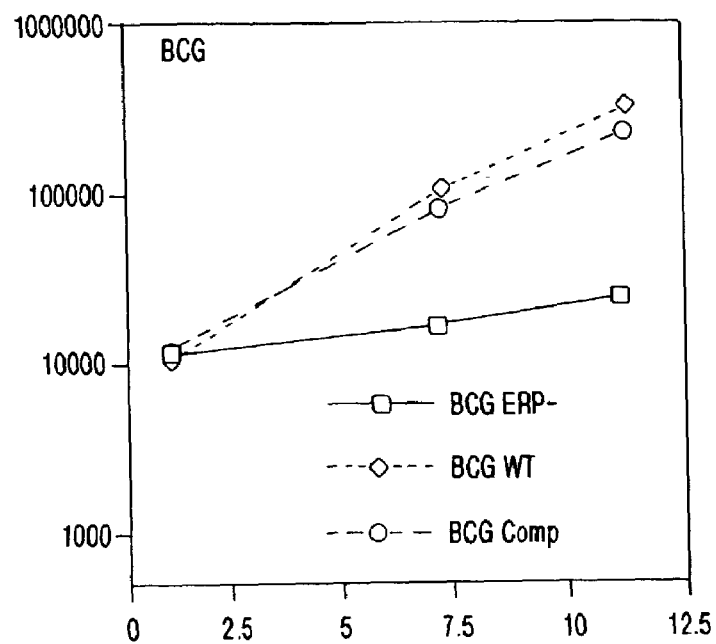
Figure 4:
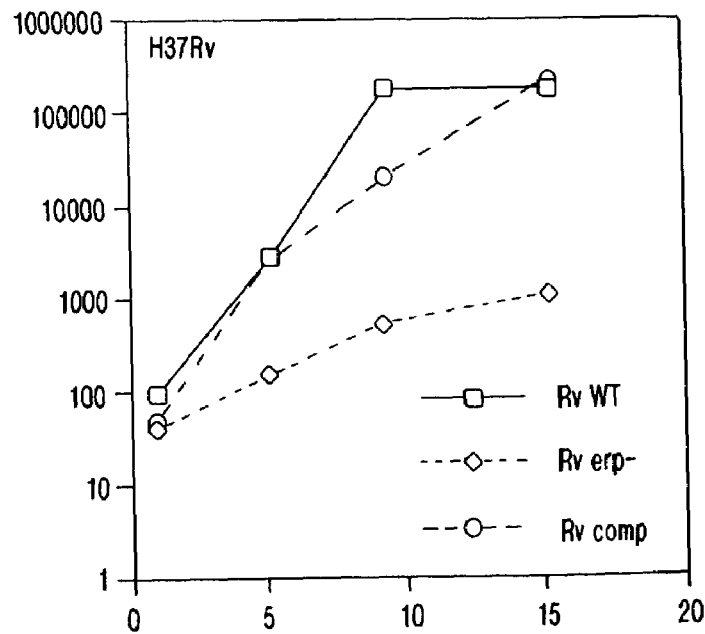

Study of the Multiplication of BCG erp::Kn in the Macrophages Derived from Mouse Medullary Precursors Previous experiments have shown that the BCG erp::Kn strain no longer persists in mice. The organ in which the elimination of BCG erp::Kn is most marked is the lung. The alveolar macrophages represent the primary target of infection by the mycobacteria of the *M. tuberculosis* complex. To specify the cell type in which the persistence of BCG erp::Kn is affected, we studied the multiplication of this strain in macrophages derived from mouse medullary precursors (BMDP). For that, BMDPs derived from the femur of 7-week old female BALB/CBYJICO mice were isolated and cultured (DMEM medium (Gibco BRL), glutamine 2 mM, fetal calf serum (Dominique Deutscher SA) 10% Vol./Vol., supernatant of L229 cells 10%) in 8-well Labtek™ chambers, at a cell density of $5 \times 10^4$ cells in 400 µl of medium. The cells were cultured for 7 days before being infected for four hours with BCG 1173 P2 (parental strain) or BCG erp::Kn (mutated strain) at a multiplicity of infection of 1. At various times post-infection (Day 0, Day 1, Day 5, Day 12, Day 17), the infected macrophages were lyzed in a buffer preserving the integrity of the mycobacteria and the lysate obtained was plated on dishes of 7H11 medium at various dilutions (from $10^0$ to $10^{-6}$). The Petri dishes were incubated at 37° C. for one month in order to measure the variation of the number of colony forming units represented in FIG. 3.

EXAMPLE 5

Study of the Delayed Hypersensitivity Reaction Induced in Guinea Pigs by BCG erp::Kn Delayed hypersensitivity reaction (DTH) reflects the induction of immune responses directed against mycobacterial components. An induration having a diameter greater than a threshold value, caused by the intradermal injection of tuberculin, signs a prior contact with mycobacteria. This test allows a rapid diagnosis of the tuberculosis infection in non-vaccinated subjects. However, this test is difficult to use in subjects vaccinated with BCG who are positive in this case. We tested the capacity of BCG erp::Kn to induce a DTH reaction. For that, two groups of 5 guinea pigs (300 g males, Dunkin Hartley strain) were immunized with $5 \times 10^5$ viable units of BCG 1173P2 or erp::Kn respectively. One month later, the same animals were immunized intradermally with the following preparations:

"purified protein derivative" (PPD)/tuberculin (WEYBRIDGE) 2 µg purified 65 kDa *M. leprae* protein 50 µg and 100 µg The diameter of the induration was measured 48 h after the injection of the different antigens on each of the 5 animals constituting the group. A positive induration greater than 8–10 mm is considered as positive.

It was observed that BCG erp::Kn induced a DTH after immunization with PPD and the 65 kD *M. leprae* protein.

EXAMPLE 6

Genotypic and Phenotypic Characterization of BCG erp::Kn

The characterization of the *M. bovis* mutant BCG erp::Kn was carried out in two ways. In a first instance, the genomic DNA of the mutant BCG (M) was extracted and analyzed by the Southern molecular hybridization technique (Berthet et al., 1995) in comparison with the genomic DNA of the parental BCG strain (P). Digestion with EcoRI indicates that the genome of BCG erp::Kn has lost such a site, located in the erp gene and destroyed by the insertion of the kanamycin cassette. Furthermore, digestion with PstI, indicates that the restriction fragment carrying erp in BCG erp::Kn comprises an insert of 1.3 kbp corresponding to the presence of the kanamycin cassette. These data confirm the replacement of the wild-type erp allele with a mutated erp::Kn allele in BCG erp::Kn.

In a second instance, the expression of the ERP protein was analyzed in the wild-type BCG and in BCG erp::Kn by immunodetection according to the so-called "Western blot" method (Sambrook et al., 1989) with the aid of an anti-ERP rabbit serum. The ERP protein is no longer detectable in the supernatant of BCG erp::Kn.

EXAMPLE 7

Preparation of the *Mycobacterium tuberculosis* H37RV Strain: H37RV erp::Kn

The H37RV erp::Kn strain is derived from the reference *Mycobacterium tuberculosis* strain. The strain has the characteristic feature of no longer producing the protein corresponding to the erp gene. The erp gene determines the synthesis of a repetitive exported protein located at the surface of the *Mycobacterium tuberculosis* complex bacteria. This strain was constructed during a homologous recombination experiment by replacing the wild-type copy of the erp gene with a mutated copy, using the plasmid pIPX56 as described above. The mutated version of the erp gene contains an insertion of a cassette conferring resistance to kanamycin at the level of the EcoRI restriction site. Such a mutation abolishes the synthesis of the gene for a functional erp protein. One of the phenotypes associated with the introduction of this mutation is the loss of the capacity to persist in mice.

EXAMPLE 8

Characterization of the Product of the *Mycobacterium tuberculosis* erp Gene To characterize the product of the *M. tuberculosis* erp gene, the recombinant ERP protein was purified and overproduced. The protein was synthesized in *E. coli* fused with 6 histidine residues (ERP-6His). ERP-6His forms cytoplasmic inclusion bodies and is then purified by immobilization on nickel affinity chromatography under denaturing conditions. Renatured, soluble ERP-6His is analyzed by a two-dimensional electrophoresis gel (Laurent-Winter, 1997).

ERP-6His is separated into two species having the same molecular weight (36 kDa) but differing as regards their isoelectric point (pI). The predominant form has a pI of 5.3 which corresponds to that calculated for ERP-6His. The minor form is more acidic (pI 5.2), is likely to correspond to an aberrant form appearing in the cytoplasm of *E. coli*. This preparation of ERP-6His was used to immunize rabbits and a polyclonal serum with a high titer was obtained. Immunoreactive bands of 36 and 34 kDa were detected by means of this serum both in the fractions associated with the cells and with the culture filtrates precipitated with TCA (trichloroacetic acid) of BCG and *M. tuberculosis* (strain Mt 103). The larger band comigrated with recombinant ERP-6His. The 34 kDa band might be the result of a proteolytic degradation or alternatively of a post-translational treatment taking place in *M. tuberculosis*. These data are in agreement with those showing that the PGLTS (SEQ ID NO: 5) antigen, an *M. bovis* protein having more than 99% identity with the *M. tuberculosis* ERP protein, is present in the form of a doublet of similar molecular weight in concentrated cellular fluids (BIGI et al., 1995).

On the basis of the structural characteristics, it has been suggested that the ERP protein may also be present at the surface of bacteria. To determine precisely the subcellular location of ERP, the attached *M. tuberculosis* bacillus was brought into contact with an anti-ERP serum and then incubated with a gold-labeled anti-rabbit conjugate. Observation by transmission electron microscopy revealed an intense surface labeling at the periphery of the bacillus, indicating that ERP is a molecule exposed at the surface. This result was confirmed by the observation of the labeled cell wall on section tubes of *M. tuberculosis* (data not shown).

It was then determined if ERP was produced during intracellular multiplication of *M. tuberculosis* inside the cultured macrophages. For this purpose, J774 mouse macrophages were infected with a clinical isolate of *M. tuberculosis* and were then observed by immunoelectron microscopy.

While no significant labeling was observed with the ERP preimmune serum, a specific labeling of the mycobacterial cell wall and of the phagosomal lumen was observed with the serum of rabbit immunized with ERP. Furthermore, small vesicles containing labeled ERP were observed in the immediate vicinity of the phagosomes. This demonstrates that ERP is produced in the phagosomes of *M. tuberculosis* and suggests that ERP moves around inside the cells.

EXAMPLE 9

Role of the ERP Protein in the Intracellular Growth of Mycobacteria

Figure 5A:
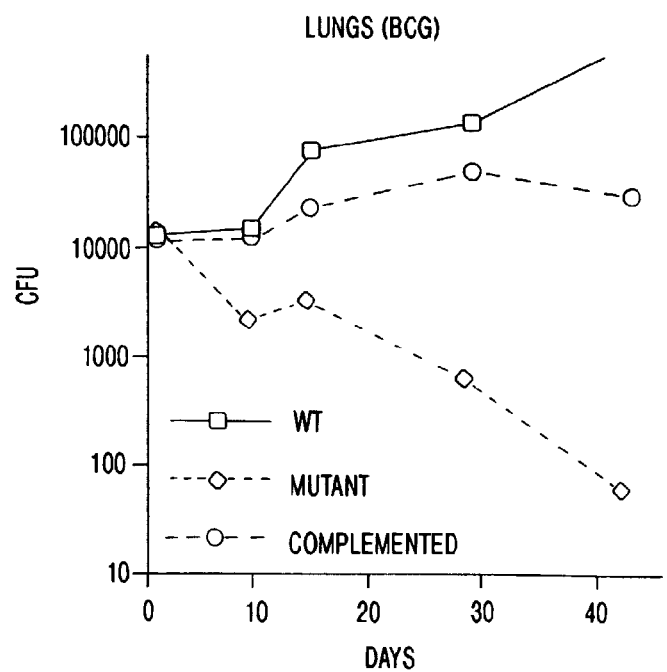
Figure 5A:
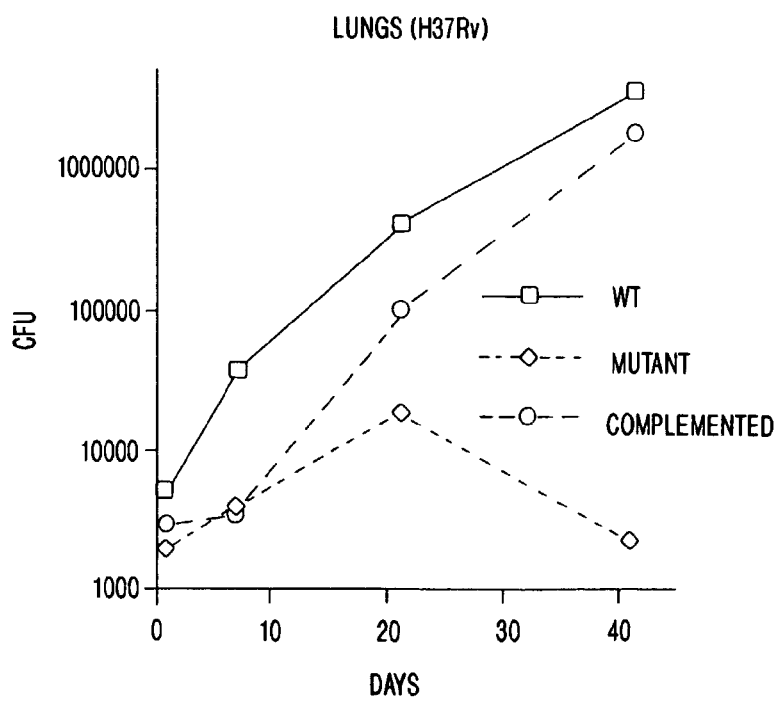
Figure 5B:
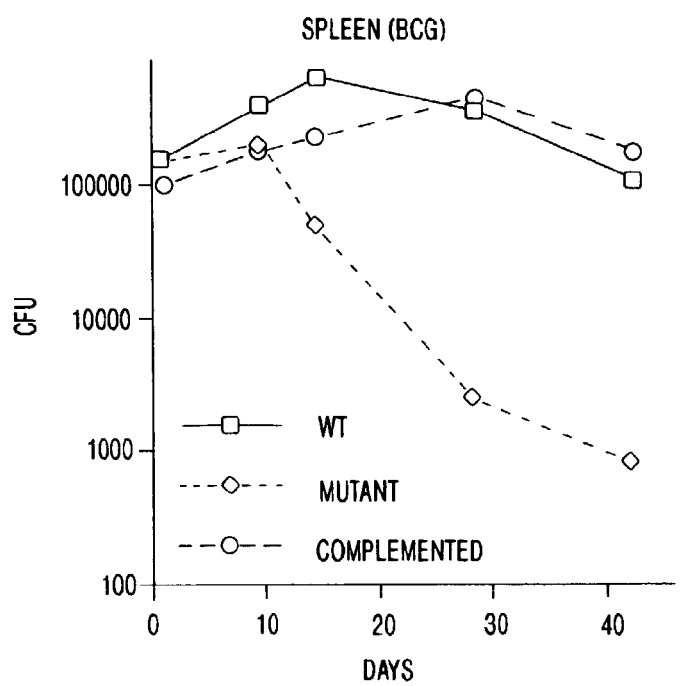
Figure 5B:
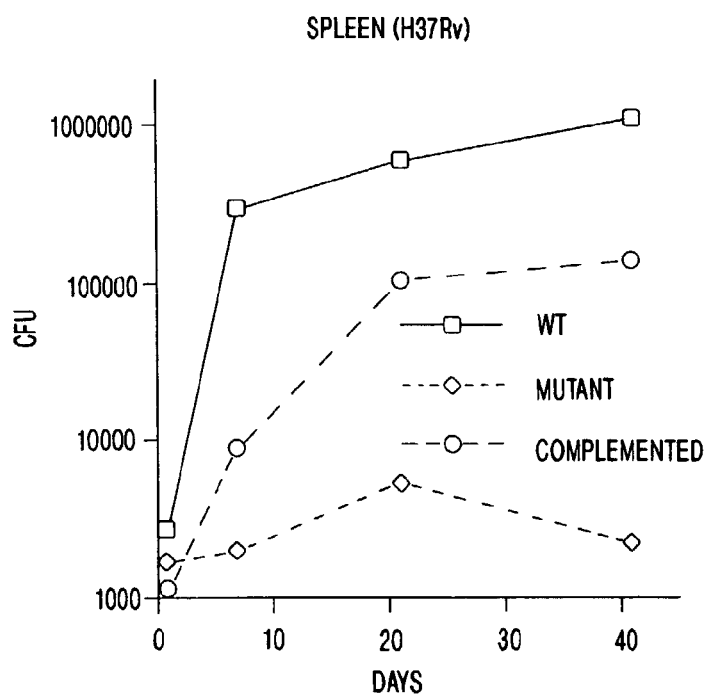
Figure 5C:
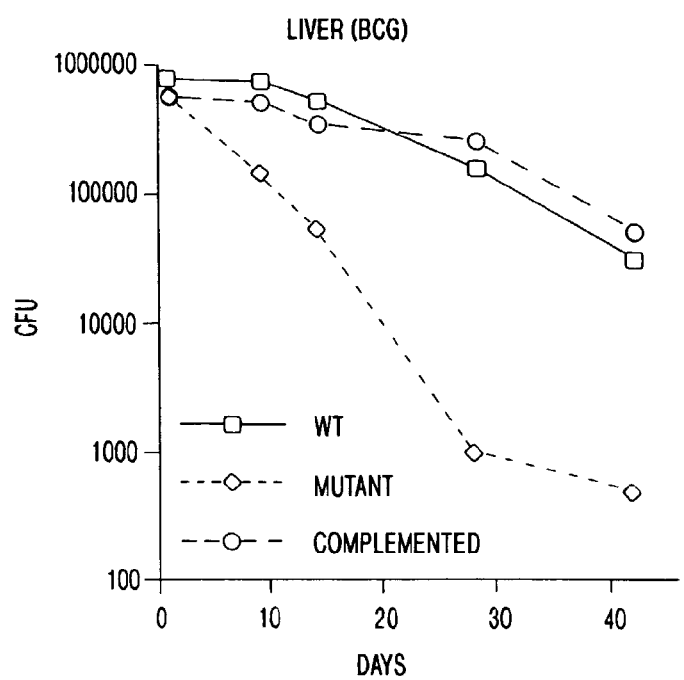
Figure 5C:
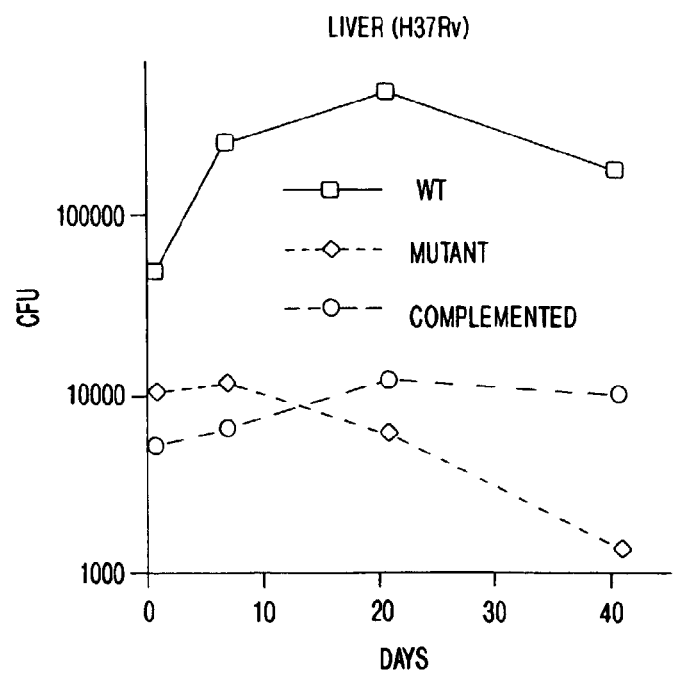

It was then examined if ERP was an essential bacteria component for the intracellular growth stage. For this purpose, a targeted null mutation was introduced into the erp locus of the *M. tuberculosis* H37Rv strain and into the *M. bovis* BCG strain and into the model vaccine strain of *M. bovis* BCG. A suicide vector which is counterselectable with sucrose, pJQ200, was used to introduce a mutant allele of erp (erp::aph) into the *M. bovis* BCG chromosome.

The corresponding *M. tuberculosis* was constructed using the ts-sacB technology (Pelisic et al., 1997).

Mutant strains resulting from alleleic exchange were called BCG erp::aph and H37Rv erp::aph. A single copy of erp was reintroduced at the attB site of BCG erp::aph and H37Rv erp::aph by means of the integrative vector derived from the mycobacteriophage MS6 (pAV6950). Analysis of the chromosomal DNA extracted from the parental strain (P), mutant strain (M) or complemented strain (complemented is understood to mean the reintroduction of a functional erp gene capable of directing the synthesis of the ERP protein) revealed that the EcoRI site cut during the construction of erp::aph was also lost in the genome of the mutant and complemented strains. Furthermore, analysis using PstI indicates an insertion of 1.3 kb inside the restriction fragment carrying erp. Hybridization of the same membrane with the sequences of the vectors pJQ200 and pPR27 did not make it possible to detect any signal (data not shown) suggesting that only the erp::aph cassette was introduced into the genome of BCG erp::aph and H37Rv erp::aph. Analysis of the fractions associated with the cells and of the concentrated supernatants from cultures of BCG erp::aph and H37Rv erp::aph indicated that the interruption of erp had abolished the production of ERP. This was confirmed by immunoelectron microscopy by the disappearance of the gold labeling on *M. bovis* BCG erp::aph cryosections. By contrast, the integration of erp at the attB site of the mutant erp::aph strains restored the production of ERP both at the surface of the cells and in the *M. tuberculosis* and *M. bovis* culture medium. Morphological analysis of the colony, doubling the length of time and the growth characteristics in the Middelbrook 7H9/ADC culture or the minimum Sauton medium, did not make it possible to identify any difference between the mutant, parental and complemented strains of BCG and H37Rv. Taken together, these data show that erp is not essential for the growth of BCG and H37Rv under laboratory conditions.

EXAMPLE 10

The capacity of BCG erp::aph and H37Rv erp::aph to grow in phagocytic cells was examined. For this purpose, the multiplication of the mutant and parental strains in a culture of macrophages derived from cellular marrow was compared. As shown in FIG. 4A, the counting of the CFUs indicates that the erp::aph mutants do not multiply inside the mouse macrophages whereas the parental and complemented strains have a normal growth. Furthermore, the H37Rv erp::aph strain shows a reduction in the cytopathic effects compared with the parental and complemented strains (FIG. 4B). To determine if the erp::aph mutation also affects multiplication inside the host, the persistence of BCG erp::aph and H37Rv erp::aph in mice was analyzed. 106 viable units of the parental strains, mutant strains erp::aph and erp-complemented strains were injected by the intravenous route into Balb/c mice and the bacterial infection was monitored by counting the CFUs after a period of 56 days (Lagranderie et al., 1996). The counting was carried out on the lungs, the liver and the spleen, three organs known to contain the highest microbacterial load after inoculation by the intravenous route. As represented in FIG. 5A, the BCG erp::aph mutants were rapidly eliminated from the lungs of the infected animals whereas the corresponding parental and complemented strains colonized this tissue and survived. By contrast, the H37Rv erp::aph mutant survived but multiplied very slowly compared with the parental and complemented strains. The lungs represent the site of infection by the members of the *M. tuberculosis* complex during tuberculosis. The multiplication of the erp::aph mutants was also greatly reduced in the liver (FIG. 5B) and the spleen (FIG. 5C). Furthermore, the morphology of the BCG colonies after having infected an animal is very different: whereas the parental BCG gives rise to a so-called "diffuse" colony morphology, BCG erp::aph no longer diffuses and shows delayed growth (up to one week compared with the parental strain). The significance of this observation is unknown but the loss of the "diffuse" phenotype was correlated with the lowest levels of residual virulence among the BCG substrains (Dubos and Pierce, 1956, Pierce and Dubos, 1956, Pierce, Dubos and Scheiffer, 1956 and Dubos and Pierce, 1956). The "nondiffuse" phenotype is not permanent and is lost after restriction of the culture medium on 7H11. Furthermore, the reintroduction of erp restores the parental phenotype. Be that as it may, these data demonstrate that the erp expression is required during the stage of intracellular growth of the mycobacteria belonging to the *M. tuberculosis* complex.

TABLE

| Origin | No. of sera tested | MBP-ERP* | ERP-His6 | 65 kDa BCG |
|---|---|---|---|---|
| Humans monitored | 4 | – | – | +/– |
| Humans (Bligny) Tuberculosis sufferers *M. tuberculosis* | 21 | – | – | + (In Pool) |
| Humans (Uganda) Tuberculosis sufferers *M. tuberculosis* | 10 | ND | +++ (3/10) | ND |
| Children (Necker) Tuberculosis sufferers *M. tuberculosis* (Direct Exam.+) | 4 | – | – | + (In Pool) |
| Humans (Madagascar) Tuberculosis sufferers *M. bovis* | 6 | – | – | + |
| Humans (Nepal) Lepromatous leprosy sufferers *M. leprae* | 1 Pool | +++ | +++ | +++ |
| Bovins Tuberculosis sufferers *M. bovis* | 4 | +++ | +++ | +++ |

*ERP protein fused with the Maltose Binding Protein The serum of the individuals tested (or the pool in the case of leprosy sufferers) was brought into contact with each of the three proteins mentioned in the table. The immune response was measured.

REFERENCES

Arruda, S., Bornfim, G., Knights, R., Huima-Byron, T. & Riley, L. W. (1993) *Science* 261:1454–1457.

Azad, A. K., Sirakova, T. D., Rogers, L. M. & Kolattukudy, P. B. (1996) *Proc. Nat. Acad. Sci. USA* 93:4787–4792.

Balasubramanian, V., Pavelka Jr., M. S., Bardarov, S. S., Martin, J., Weisbrod, T. R., McAdam, R. A., Bloom, B. R. & Jacobs Jr., W. R. (1996) *J. Bacteriol.* 178:273–279.

Balasuc A.-M., Deriaud E., Leclerc C. D., Georghiu M. *Infect. Immunn.* 64, 1 (1996).

Berthet, F. X., Rauzier J., Lim, E. M., Philipp, W., Gicquel B. and D. Portnoi (1995) Characterization of the *Mycobacterium tuberculosis* erp gene encoding a potential cell surface protein with repetitive structures. *Microbiology* 141:2123–2310.

Bigi F., Alito A., Fisanotti J. C., Romano M. I., Cataldi A., *Infect. Immun.* 63, 2581 (1995).

Bloom, B. R. & Murray, C. J. L. (1992) *Science* 257: 1055–1064.

Chastellier de C., Lang T., Thilo L., Eur. J. Cell Biol. 68, 167 (1995).

Collins, D. M., Kawakami, R. P., de Lisle, G. W., Pascopella, L., Bloom, B. R. & Jacobs Jr., W. R. (1995) *Proc. Nat. Acad. Sci. USA* 92:8036–8040.

Curtiss, III, Roy, (1990) *New Generation Vaccines*, pp. 161–165.

Dooley, S. W., Jarvis, W. R., Martone, W. J. and D. E. Snider (1992). Multidrug resistant tuberculosis. *Ann. Intern. Med.* 117:257–259.

Dubos R. J., Pierce C. H., *Amer. Rev. Tuberc.* 74, 655–666, (1956).

Dubos R. J., Pierce C. H., ibid. 74, 699–717, (1956).

Falkow, S. (1988) *Rev. Infect. Dis.* 10:5274–5276.

Guilhot, C., Otal, I., van Rompaey, I., Martin, C. & Gicquel, B. (1994) *J. Bacteriol.* 176:535–539.

Hoiseth, Susan K. & Stocker, B. A. D., (1981) *Nature,* 291:238–239.

Jacobs Jr, W. R. (1992) *Immunobiol.* 184:147–156.

Lagranderie M. R., Balazuc A.-M., Deriaud E., Leclerc C. D., Georghiu M., *Infect. Immun.* 64, 1 (1996).

Laurent-Winter C., Ngo S., Danchin A., Bertin P., *Eur. J. Biochem.* 244, 767 (1997).

Levin, M. M., Herrington, D., Murphy, J. R., Morris, J. G., Losonsky, G., Tall, B., Lindberg, A.

Norman, B., Dellagostin, O. A., McFadden, J. & Dale, J. W. (1995) *Mol. Microbiol.* 16:755–760.

Noriega, Fernando R., Wang, J. Y., Losonsky, G., Maneval D. R., Hone, D. M. & Levin, M. M., (1994) *Infect. Immun.,* 62 (11):5168–5172.

Oyston, P. C. F., Willimson, E. D., Leary, S. E. C., Eley, S. M., Griffin, K. F. & Titball, R. W., (1995) *Infect. Immun.,* 63(2):563–568.

Pascopella, L., Collins, F. M., Martin, J. M., Lee, M. H., Hatftill, G. F., Stover, C. K., Bloom, B. R. & Jacobs Jr, W. R. (1994) *Infect. Immun.* 62:1313–1319.

Pelicic, V., Reyrat, J.-M. & Gicquel, B. (1996) FEMS *Microbial. Lett.* 144:161–166.

Pelicic V., Jackson M., Reyrat J. M., Jacobs W. R., Gickel B. and Guilhot C., 1997, *Efficient allelic exchange and transposon mutagenesis in M. tuberculosis, PROC. NATL. ACAD. SCIE. USA*, vol. 94, 10955–10960.

Pierce C. H., Dubos R. J., ibid. 74, 667–682, (1956).

Pierce C. H., Dubos R. J., Schaefer W. B., ibid. 74, 683–698, (1956).

Reyrat, J.-M., Berthet, F.-X. & Gicquel, B. (1995) *Proc. Nat. Acad. Sci. USA* 92:8768–8772.

Sambrook, J. Fritsch, E. F., and T. Maniatis. 1989. *Molecular cloning: a laboratory manual.* 2ed. Cold Spring Harbor Laboratory, Cold Spring Harbor, N.Y.

Sambrook J., Fritsch E. F., Maniatis T., *Molecular cloning: a laboratory manual* (Cold Spring Harbor Laboratory Press, 1987) pp. 18.47–18.74 [second edition].

Straley, Susan C. and Harmon, Paula A, (1984) *Infection and Immunity,* 45(3):649–654.

Sudre, P., Ten Dam, G. and A. Kochi (1992). Tuberculosis in the world today. *Bull. WHO* 70(3):297–308.

The invention claimed is:

1. A *Mycobacterium* strain comprising a modified erp gene in its genome, wherein the strain is a strain selected from the complex of *Mycobacterium tuberculosis* species.

2. The *Mycobacterium* strain according to claim 1, wherein the strain is recombinant.

3. The *Mycobacterium* strain according to claim 1 or 2, wherein the erp gene is modified by mutation, insertion, deletion, or substitution.

4. The *Mycobacterium* strain according to claim 3, wherein the mutation, insertion, deletion, or substitution is carried out on at least two base pairs.

5. The *Mycobacterium* strain according to claim 3, wherein the erp gene is modified by insertion of a nucleotide or polynucleotide.

6. The *Mycobacterium* strain according to claim 5, wherein the inserted polynucleotide comprises a selectable gene.

7. The *Mycobacterium* strain according to claim 6, wherein the selectable gene imparts resistance to an antibiotic.

8. The *Mycobacterium* strain according to claim 7, wherein the antibiotic is kanamycin, spectinomycin, or hygromycin.

9. The *Mycobacterium* strain according to claim 1, wherein the strain is capable of expressing a polynucleotide encoding an antigen of a *Mycobacterium* of a species other than that to which said strain belongs.

10. The *Mycobacterium* strain according to claim 1, wherein the strain is capable of expressing a polynucleotide foreign to the *Mycobacterium* genus.

11. A *Mycobacterium* strain according to claim 3, wherein the erp gene lacks its repeat sequences.

12. An immunogenic composition comprising a *Mycobacterium* strain according to claim 1, wherein the composition is in a form suitable for administration to a human or an animal, and wherein the *Mycobacterium* strains is presented in an amount sufficient to induce an inmune response in the human or animal when the composition is administered.

13. A method for the production of a *Mycobacterium* strain with an erp gene in its genome, wherein the erp gene is modified, and wherein the strain is a strain selected from the complex of *Mycobacterium tuberculosis* species, comprising:

transforming, with a vector comprising a modified erp gene, a *Mycobacterium* strain of the complex of *Mycobacterium tuberculosis* species propagated at a permissive temperature, culturing colonies resulting from the transformation on a medium supplemented with a selectable product and sucrose, and isolating the strain thus selected.

14. The method according to claim 13, wherein the selectable product is an antibiotic chosen from kanamycin, spectinomycin and hygromycin.

15. An immunogenic composition comprising a *Mycobacterium* strain obtained using the method according to claim 14.

16. The immunogenic composition of claim 15, further comprising at least one pharmaceutically compatible excipient.

17. An immunogenic composition comprising a *Mycobacterium* strain obtained using the method according to claim 13.

18. The immunogenic composition of claim 17, further comprising at least one pharmaceutically compatible excipient.

19. A method of screening individuals, to whom an immunogenic composition according to claim 16 or claim 18 has been administered, comprising detecting an absence, from a biological sample from said individuals, of antibodies directed against a whole or part of a purified ERP protein.

20. A method of screening individuals, to whom an immunogenic composition according to claim 16 or claim 18 as been administered, comprising detecting, in a biological sample from said individuals, T cells directed against a whole or part of a purified ERP protein.

21. A method of preparing a *Mycobacterium* strain according to claim 1, comprising:

providing a recombinant vector comprising a modified erp gene, and combining said recombinant vector with a *Mycobacterium* strain of the complex of *Mycobacterium tuberculosis* species comprising an erp gene, under conditions where allelic exchange can occur, wherein allelic exchange results in replacement of said erp gene with said recombinant vector.

* * * * *

UNITED STATES PATENT AND TRADEMARK OFFICE
CERTIFICATE OF CORRECTION

PATENT NO. : 7,160,548 B2  Page 1 of 1
APPLICATION NO. : 10/259460
DATED : January 9, 2007
INVENTOR(S) : Brigitte Gicquel and Francois-Xavier Berthet It is certified that error appears in the above-identified patent and that said Letters Patent is hereby corrected as shown below:

On the title page, item (73), "Institit" should read --Institut--.

In claim 12, column 19, lines 37-38, "strains is presented" should read --strain is present--.

In claim 20, column 20, line 31, "as" should read --has--.

Signed and Sealed this

Twenty-seventh Day of March, 2007

JON W. DUDAS
*Director of the United States Patent and Trademark Office*